US010198814B2

United States Patent
Iwase et al.

(10) Patent No.: US 10,198,814 B2
(45) Date of Patent: Feb. 5, 2019

(54) IMAGE PROCESSING DEVICE AND IMAGE PROCESSING METHOD

(71) Applicant: CANON KABUSHIKI KAISHA, Tokyo (JP)

(72) Inventors: Yoshihiko Iwase, Yokohama (JP); Makoto Sato, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 9 days.

(21) Appl. No.: 15/411,149

(22) Filed: Jan. 20, 2017

(65) Prior Publication Data

US 2017/0221203 A1    Aug. 3, 2017

(30) Foreign Application Priority Data

Jan. 29, 2016  (JP) .................................. 2016-016366

(51) Int. Cl.
| | |
|---|---|
| G06K 9/00 | (2006.01) |
| G06T 7/00 | (2017.01) |
| G06K 9/46 | (2006.01) |
| A61B 3/00 | (2006.01) |
| A61B 3/10 | (2006.01) |
| A61B 8/13 | (2006.01) |

(52) U.S. Cl.
CPC .......... *G06T 7/0012* (2013.01); *A61B 3/0025* (2013.01); *A61B 3/102* (2013.01); *G06K 9/0061* (2013.01); *G06K 9/00617* (2013.01); *G06K 9/4661* (2013.01); *G06T 2207/10101* (2013.01); *G06T 2207/30041* (2013.01)

(58) Field of Classification Search
CPC .................................. A61B 5/00; G06T 7/00
USPC ................... 382/128–134; 600/443
See application file for complete search history.

(56) References Cited

U.S. PATENT DOCUMENTS

| | | | |
|---|---|---|---|
| 8,718,672 B2 * | 5/2014 | Xie ........................ | G01C 22/00 455/404.1 |
| 8,830,462 B2 * | 9/2014 | Ishimaru ................ | G01N 21/23 356/365 |
| 8,977,522 B2 * | 3/2015 | Jallon .................... | A61B 5/112 703/2 |

FOREIGN PATENT DOCUMENTS

WO    2010122118 A1    10/2010

OTHER PUBLICATIONS

Zotter, S., et al., "Measuring Retinal Nerve Fiber Layer Birefringence, Retardation, and Thickness Using Wide-Field, High-Speed Polarization Sensitive Spectral Domain OCT", Investigative Ophthalmology & Visual Science, Jan. 7, 2013, pp. 72-84. vol. 54, No. 1, The Association for Research in Vision and Ophthalmology, Inc., U.S.A.

* cited by examiner

*Primary Examiner* — Abolfazl Tabatabai
(74) *Attorney, Agent, or Firm* — Canon U.S.A., Inc. IP Division

(57) ABSTRACT

An image processing device includes: a signal processing unit configured to generate phase retardation information of a subject eye by using information about a plurality of lights obtained by dividing, into lights of different polarizations, a light obtained by combining a light returned from the subject eye irradiated with a measurement light and a reference light corresponding to the measurement light; and a detection unit configured to detect a region in which a change amount of the phase retardation information in a depth direction of the subject eye is larger than a threshold value.

18 Claims, 12 Drawing Sheets

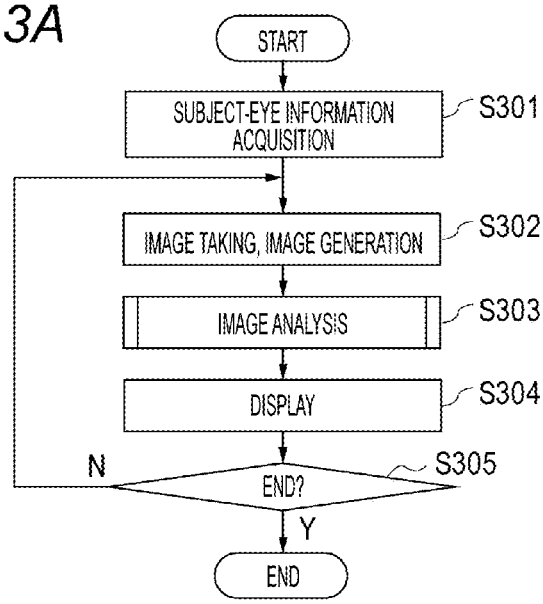
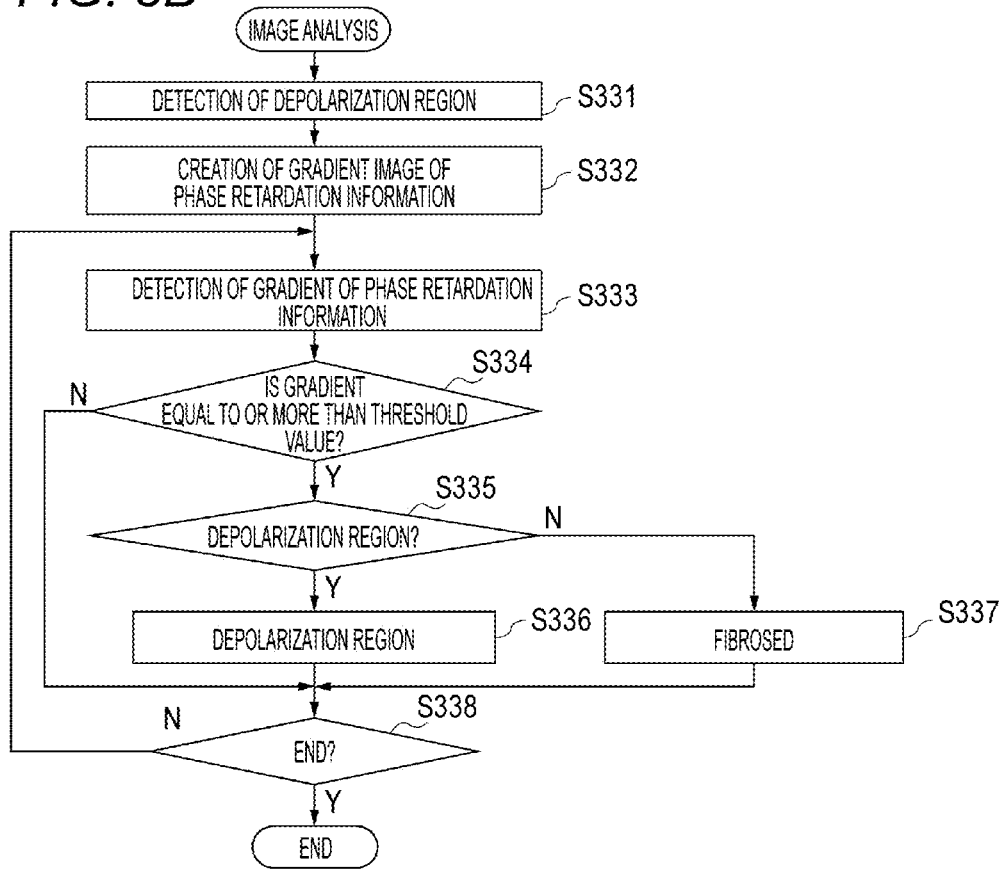

IMAGE PROCESSING DEVICE AND IMAGE PROCESSING METHOD

BACKGROUND OF THE INVENTION

Field of the Invention

The present invention relates to an image processing device and an image processing method of processing polarization tomographic images of a subject eye.

Description of the Related Art

Optical coherence tomography (Optical Coherence Tomography: hereinafter, OCT) utilizing multiple-wavelength optical-wave interference is capable of obtaining tomographic images of a sample (particularly, eye fundus) at high resolution.

Recently, with an ophthalmic OCT device, there have been attempts to acquire functional OCT images which image optical characteristics, movement, etc. of eye-fundus tissues in addition to normal OCT images which image the shapes of the eye-fundus tissues.

Polarization OCT which is one of functional OCT carries out imaging by using polarization parameters, which are one of the optical characteristics of the eye-fundus tissues.

The polarization OCT is capable of forming polarization OCT images and carrying out discrimination and segmentation of eye-fundus tissues by utilizing the polarization parameters. The polarization OCT uses the light modulated to circularly polarized light as the measurement light to observe a sample, detects interference light divided as two orthogonal linearly polarized light, and generates a polarization OCT image (see International Publication No. 2010/122118).

In Invest Ophthalmol Vis Sci. 2013 Jan. 7, Zotter, S., et al. "Measuring retinal nerve fiber layer birefiringence, retardation, and thickness using wide-field, high-speed polarization sensitive spectraldomain OCT", Retardation (phase retardation) and Birefringence (birefringence) obtained from the polarization OCT are obtained. In this case, the birefringence is obtained from a Retardation value in RNFL extracted from Intensity (luminance) image and the thickness of RNFL. Note that, in the polarization OCT image, polarization parameters (Intensity, Retardation, Axis Orientation (fast-axis orientation), DOPU (polarization degree), etc.) are imaged.

SUMMARY OF THE INVENTION

According to an aspect of the present invention, an image processing device includes a signal processing unit and a detection unit, with the signal processing unit being configured to generate phase retardation information of a subject eye by using information about a plurality of lights obtained by dividing, into lights of different polarizations, a light obtained by combining a light returned from the subject eye irradiated with a measurement light and a reference light corresponding to the measurement light, and with the detection unit being configured to detect a region in which a change amount of the phase retardation information in a depth direction of the subject eye is larger than a threshold value.

Further features of the present invention will become apparent from the following description of exemplary embodiments (with reference to the attached drawings).

BRIEF DESCRIPTION OF THE DRAWINGS

FIGS. 3A and 3B show process flows in the first embodiment.

DESCRIPTION OF THE EMBODIMENTS

In a polarization OCT image, polarization parameters (Intensity, Retardation, Axis Orientation (fast-axis orientation), DOPU (polarization degree), etc.) are imaged.

Herein, it is difficult to understand above described various polarization OCT images unless a viewer is get used to it. For example, fiber regions of RNFL (nerve fiber layer) or Fibrosis (fibrosis) have birefringence. A Retardation image converts a phase retardation amount caused by the birefringence thereof to an image. Herein, Retardation is a polarization parameter dependent on the distance of a depth direction of a subject eye. Therefore, the Retardation image is an image in which the boundary of the above described fibrosed region is difficult to understand.

Beneficially, according to an aspect of the present invention, a fibrosed region of a polarization tomographic image of a subject eye can be displayed so that the region can be easily distinguished.

First Embodiment

A first embodiment will be described in detail by using drawings.

[Overall Configuration of Device]

Figure 1:
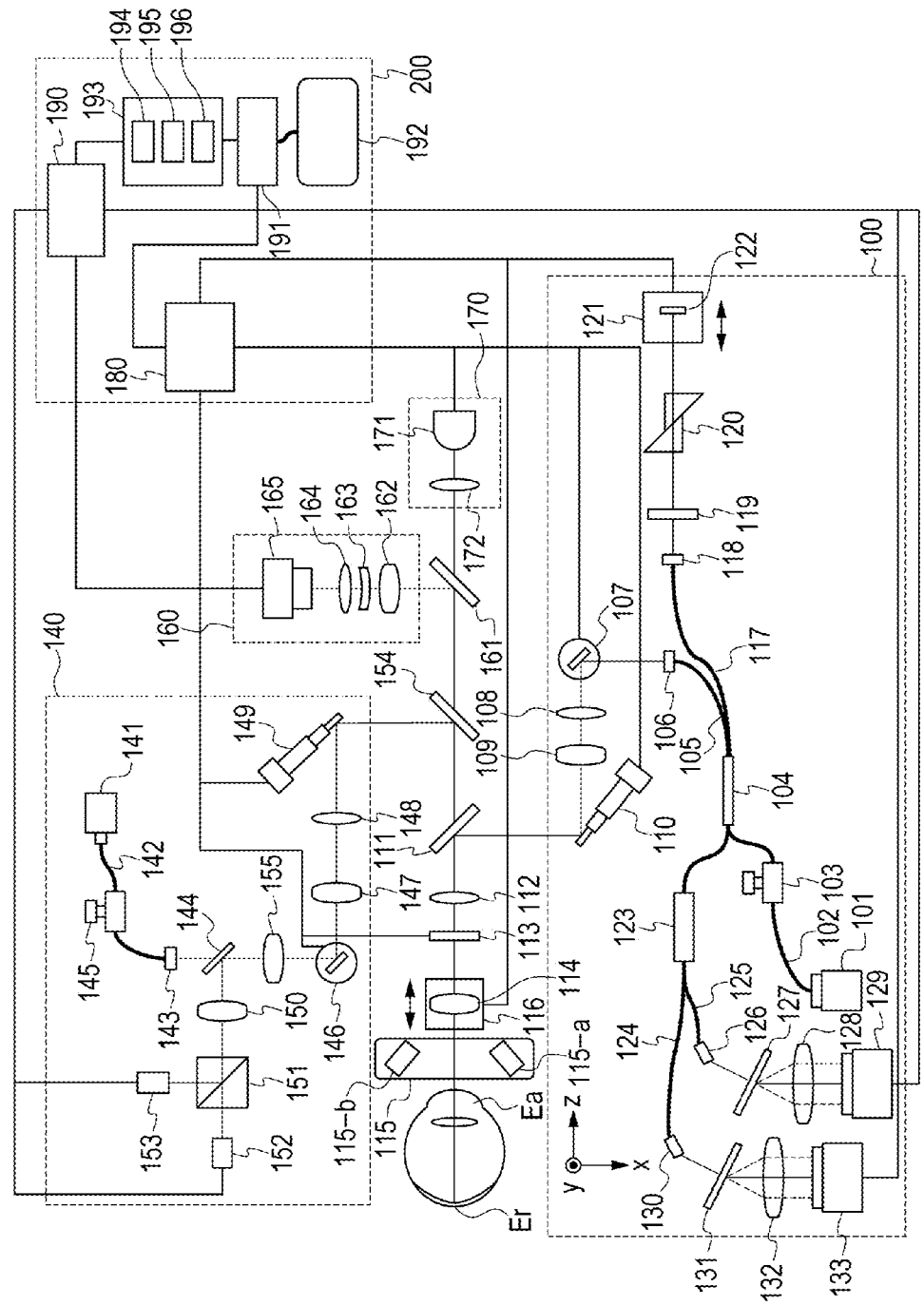
FIG. 1 is a schematic view of an entire configuration of an image processing device in a first embodiment.

FIG. 1 is a schematic view of an overall configuration of an image processing device of the present embodiment.

The embodiment includes a polarization OCT (Polarization Sensitive OCT; hereinafter, PS-OCT) 100, a scanning-type ophthalmoscope utilizing polarization (Polarization Sensitive Scanning Laser Ophthalmoscope: hereinafter, PS-SLO) 140, an anterior-eye-portion image-pickup unit 160, an interior fixation lamp 170, and a control unit 200.

In a state in which the interior fixation lamp 170 is lit to cause a subject eye to focus thereon, alignment of the device is carried out by using an image of the subject eye observed by the anterior-eye-portion image-pickup unit 160. After the alignment is completed, an image of an eye fundus by the PS-OCT 100 and the PS-SLO 140 is taken.

<Configuration of PS-OCT 100>

A configuration of the PS-OCT 100 will be described.

A light source 101 is a SLD light source (Super Luminescent Diode), which is a low-coherence light source, and emits, for example, light having a central wavelength of 850 nm and a bandwidth of 50 nm. SLD was used as the light source 101, but any light source that can emit low-coherence light such as an ASE light source (Amplified Spontaneous Emission) may be used.

The light emitted from the light source 101 is guided to a fiber coupler 104, which has a polarization maintaining function, via a PM (Polarization Maintaining) fiber 102 and a polarization controller 103 and is branched into measurement light (also referred to as OCT measurement light) and reference light (also referred to as reference light corresponding to OCT measurement light).

The polarization controller 103 adjusts the state of polarization of the light emitted from the light source 101 and adjusts that to linear polarization. The branch ratio of the fiber coupler 104 is 90 (reference light):10 (measurement light).

The branched measurement light is emitted as parallel light from a collimator 106 via a PM fiber 105. The emitted measurement light reaches a dichroic mirror 111 via an X-scanner 107 including a galvano-mirror, which scans the measurement light at an eye fundus Er in a horizontal direction, lenses 108 and 109, and a Y-scanner 110 including a galvano-mirror, which scans the measurement light at the eye fundus Er in a vertical direction. The X-scanner 107 and the Y-scanner 110 are controlled by a drive control unit 180 and are capable of scanning desired ranges (also referred as acquisition ranges of tomographic images, acquisition positions of tomographic images, irradiation positions of measurement light) of the eye fundus Er by the measurement light. The dichroic mirror 111 has characteristics to reflect the light of 800 nm to 900 nm and allow the light other than that to transmit therethrough.

The measurement light reflected by the dichroic mirror 111 passes through a λ/4 polarizing plate 113 (an example of polarization adjusting member), which is installed to be tilted by 45°, via a lens 112; and, as a result, the phase thereof is shifted by 90°, and the measurement light undergoes polarization control into the light of circularly polarized light. Note that the tilt of the λ/4 polarizing plate 113 is preferred to be, for example, the angle corresponding to the tilt from the optical axis of a polarization dividing surface of the fiber coupler 123 incorporating a polarizing beam splitter (an example of a disposition state).

Note that it is preferred that the λ/4 polarizing plate 113 be configured to be able to be inserted into or removed from an optical path. For example, a mechanical configuration in which the λ/4 polarizing plate 113 is rotated by using an axis parallel to the optical axis as a rotation axis is conceivable. By virtue of this, a small device in which a SLO optical system and a PS-SLO optical system can be easily switched can be realized. Also, the small device in which an OCT optical system and a PS-OCT optical system can be easily switched can be realized.

Herein, the light which enters the subject eye undergoes the polarization control to the light of circularly polarized light since the λ/4 polarizing plate 113 is installed to be tilted by 45°; however, there is a case in which circularly polarized light is not obtained at the eye fundus Er due to the characteristics of the subject eye. Therefore, the tilt of the λ/4 polarizing plate is configured to be finely adjustable by the control of the drive control unit 180.

The measurement light, which has undergone the polarization control to the circularly polarized light, is caused to focus on a retina layer of the eye fundus Er by a focus lens 114, which is placed on a stage 116, via an anterior eye portion Ea, which is a subject. The measurement light radiated to the eye fundus Er is reflected/scattered by each retina layer and is returned through the above optical path to the fiber coupler 104.

On the other hand, the reference light branched by the fiber coupler 104 is emitted as parallel light from a collimator 118 via a PM fiber 117. The emitted reference light is subjected to a λ/4 polarizing plate 119, which is installed to be tilted, from P-polarization to 22.5° S-polarization as well as the measurement light. The reference light is reflected by a mirror 122 on a coherence gate stage 121 via a dispersion compensation glass 120 and is returned to the fiber coupler 104. Since the reference light passes through the λ/4 polarizing plate 119 two times, the light of linear polarization is returned to the fiber coupler 104.

The coherence gate stage 121 is controlled by the drive control unit 180 to support, for example, differences in the eye axial lengths of subjects.

The measurement light and the reference light returned to the fiber coupler 104 become interference light through combining, is caused to enter the fiber coupler 123 incorporating the polarizing beam splitter, is divided into the light of different polarization directions (in the present embodiment, the light of P-polarization and the light of S-polarization) by a branch ratio of 50:50.

The light of the P-polarization is dispersed by a grating 131 via a PM fiber 124 and a collimator 130 and is received by a lens 132 and a line camera 133. Similarly, the light of the S-polarization is dispersed by a grating 127 via a PM fiber 125 and a collimator 126 and is received by a lens 128 and a line camera 129. Note that it goes without saying that the gratings 127 and 131 and the line cameras 129 and 133 are disposed to match the directions of polarization.

The light received by the line cameras 129 and 133 is output as electric signals corresponding to intensities of the light and is received by a signal processing unit 190.

The λ/4 polarizing plate 113 adjusts the tilt thereof based on the polarizing beam splitter, but may adjust the tilt with respect to the straight line connecting an optic disk center of the eye fundus and a macula center. Even when the polarizing beam splitter and the λ/4 polarizing plates 113 and 119 are adjusted based on a perpendicular direction as a polarization reference, similar effects are obtained.

<Configuration of PS-SLO 140>

A configuration of the PS-SLO 140 will be described.

A light source 141 is a semiconductor laser and, in the present embodiment, for example, emits light having a central wavelength of 780 nm. The measurement light (also referred to as SLO measurement light) emitted from the light source 141 is subjected to polarization control by a polarization controller 145 so as to become linear polarization via a PM fiber 142 and is emitted as parallel light from a collimator 143. The emitted measurement light passes through a perforated portion of a perforated mirror 144 and reaches a dichroic mirror 154 via a lens 155, an X-scanner 146 including a galvano-mirror, which scans the measurement light at the eye fundus Er in the horizontal direction, lenses 147 and 148, and a Y-scanner 149 including a galvano-mirror, which scans the measurement light at the eye fundus Er in the vertical direction. The X-scanner 146 and the Y-scanner 149 are controlled by the drive control unit 180 and are capable of scanning desired ranges on the eye fundus by the measurement light. The dichroic mirror 154 has characteristics to reflect 760 nm to 800 nm and allow the light other than that to transmit therethrough.

The measurement light of linear polarization reflected by the dichroic mirror 154 reaches the eye fundus Er via an optical path similar to that of the PS-OCT 100.

The measurement light radiated to the eye fundus Er is reflected/scattered by the eye fundus Er and reaches the perforated mirror 144 through the above described optical path. The light reflected by the perforated mirror 144 is divided into the light of different polarization directions (in the present embodiment, the light of P-polarization and the light of S-polarization) by a polarizing beam splitter 151 via a lens 150, is received by avalanche photodiodes (hereinafter, APD) 152 and 153, are converted to electric signals, and are received by the signal processing unit 190.

Herein, the position of the perforated mirror 144 is conjugated with a pupil position of the subject eye, and the light which has passed through a pupil peripheral portion among the reflected/scattered light of the measurement light radiated to the eye fundus Er is reflected by the perforated mirror 144.

In the present embodiment, both of the PS-OCT and PS-SLO used PM fibers. However, even with single-mode fibers (SMF), similar configurations and effects are obtained by controlling polarization by using a polarization controller.

<Anterior-Eye-Portion Image-Pickup Unit 160>

The anterior-eye-portion image-pickup unit 160 will be described.

The anterior-eye-portion image-pickup unit 160 irradiates the anterior eye portion Ea by an illumination light source 115 including LEDs 115-a and 115-b, which emit illumination light having a wavelength of 1000 nm. The light reflected by the anterior eye portion Ea reaches a dichroic mirror 161 via the lens 114, the polarizing plate 113, the lens 112, the dichroic mirrors 111 and 154. The dichroic mirror 161 has characteristics to reflect the light of 980 nm to 1100 nm and allow the light other than that to transmit therethrough. The light reflected by the dichroic mirror 161 is received by an anterior-eye-portion camera 165 via lenses 162, 163, and 164. The light received by the anterior-eye-portion camera 165 is converted to electric signals and is received by the signal processing unit 190.

<Interior Fixation Lamp 170>

The interior fixation lamp 170 will be described.

The interior fixation lamp 170 includes an interior-fixation-lamp display unit 171 and a lens 172. As the interior-fixation-lamp display unit 171, a plurality of light emitting diodes (LD) disposed in a matrix pattern are used. The lighting positions of the light emitting diodes are changed depending on the part to be subjected to image pickup by the control of the drive control unit 180. The light from the interior-fixation-lamp display unit 171 is guided to the subject eye via the lens 172. The light emitted from the interior-fixation-lamp display unit 171 is 520 nm, and a desired pattern is displayed by the control unit 180.

<Control Unit 200>

The control unit 200 for controlling the present embodiment will be described.

The control unit 200 includes the drive control unit 180, the signal processing unit 190, a display control unit 191, and a display unit 192.

The drive control unit 180 controls units in the above described manner.

The signal processing unit 190 generates images based on the signals output from the line cameras 129 and 133, the APDs 152 and 153, and the anterior-eye-portion camera 165.

An image analyzing unit 193 includes an image generating unit 194, a detection unit 195, and a judgement unit 196, generates characteristic images for carrying out image processing from the images processed by the signal processing unit 190, detects and judges the characteristics thereof, and generates visualized information of the judgement results. Note that details such as generation, analysis, etc. of images will be described later.

The display control unit 191 causes images, etc. of the images generated by the image generating unit and acquired by an eye-fundus-image acquiring unit (not shown) and a tomographic-image acquiring unit (not shown) to be displayed by a display screen of the display unit 192 (for example, a display such as liquid crystal). Note that the image data generated by the signal processing unit 190 may be transmitted by wire or wirelessly transmitted to the display control unit 191. In the present embodiment, the image processing device is described. However, as an ophthalmic apparatus or an ophthalmic system according to another embodiment of the present invention, it may be configured so that the eye-fundus-image acquiring unit includes the SLO optical system and the tomographic-image acquiring unit includes the OCT optical system.

The display unit 192 displays a display form which shows various information as described later under the control of the display control unit 191. Note that the image data from the display control unit 191 may be transmitted by wire or transmitted wirelessly to the display unit 192. The display unit 192, etc. are included in the control unit 200, but the present invention is not limited thereto, and they may be provided to be separated from the control unit 200. Also, a device portable by a user (tablet) in which the display control unit 191 and the display unit 192 are integrally formed may be employed. In that case, it is preferred to equip the display unit with a touch panel function so that operations such as movement of a display position of an image on the touch panel, enlargement/reduction, and changes of the displayed image can be carried out.

[Signal Processing]

Next, image generation in the signal processing unit 190 will be described.

<Tomographic Image Generation and Eye-Fundus Image Generation>

The signal processing unit 190 carries out reconstruction processing, which is used in general SD-OCT (Spectral Domain OCT), with respect to interference signals output from the line cameras 129 and 133, to generate two tomographic images based on polarization components (also referred to as a tomographic image corresponding to first polarization and a tomographic image corresponding to second polarization).

First, the signal processing unit 190 carries out fixed pattern noise removal from the interference signal. The fixed pattern noise removal is carried out by extracting fixed pattern noise by averaging a plurality of detected A-scan signals and subtracting that from the input interference signal.

Then, the signal processing unit 190 converts the interference signal from wavelength to wavenumber and generates a tomographic signal (also referred to as a tomographic signal representing a polarization state) by carrying out Fourier transformation.

Two tomographic images are generated by carrying out the above described process with respect to the interference signal having two polarization components.

The signal processing unit 190 generates two eye-fundus images (also referred to as an eye-fundus image corresponding to first polarization and an eye-fundus image corresponding to second polarization) based on the polarization components by aligning the signals output from the APDs 152 and 153 in synchronization with the drive of the X-scanner 146 and the Y-scanner 149.

<Luminance Image Generation> the signal processing unit 190 generates a luminance image from the above described two tomographic signals. The luminance image is basically the same as a tomographic image of a conventional OCT, and the pixel value r thereof is calculated by Expression 1 from tomographic signals $A_H$ and $A_V$ obtained from the line sensors 129 and 133.

$$r=\sqrt{A_H^2+A_V^2} \quad \text{(Expression 1)}$$

Similarly, an eye-fundus luminance image is generated from two eye-fundus images.

Figure 2A:
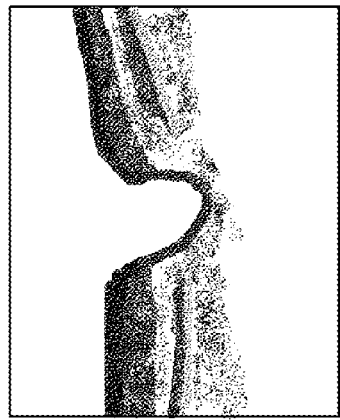
FIGS. 2A to 2E show examples of images generated by a signal processing unit in the first embodiment.

FIG. 2A shows an example of a luminance image of an optic disk portion.

<Retardation Image Generation>

The signal processing unit 190 generates a Retardation image from tomographic images of the polarization components orthogonal to each other.

The value δ of each pixel of the Retardation image is the numerically-converted phase difference between a vertical polarization component and a horizontal polarization component at the position of each pixel constituting the tomographic image and is calculated by Expression 2 from the tomographic signals $A_H$ and $A_V$.

$$\delta = \arctan\left[\frac{A_V}{A_H}\right] \quad \text{(Expression 2)}$$

Figure 2B:
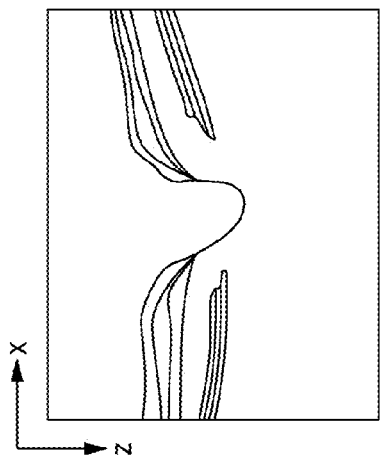

FIG. 2B shows an example of a Retardation image (also referred to as a tomographic image showing phase differences of polarization) of an optic disk portion generated in this manner, and this can be obtained by calculating Expression 2 with respect to each B-scan image. FIG. 2B shows by colors the part at which phase differences are generated in the tomographic image; wherein dense shading locations represent small phase differences, and sparse shading locations represent large phase differences. Therefore, layers with birefringence can be perceived by generating the Retardation image.

<Retardation Map Generation>

The signal processing unit 190 generates a Retardation map from the Retardation images obtained with respect to a plurality of B-scan images.

First, the signal processing unit 190 detects the retinal pigment epithelium (RPE) in each B-scan image. Since RPE has a property to depolarize, each A-scan is subjected to checking of the distribution of Retardation from an internal limiting membrane (ILM) along the depth direction within the range not including RPE, and the highest value thereof is used as a representative value of Retardation in the A-scan.

The signal processing unit 190 generates a Retardation map by carrying out the above described process with respect to all Retardation images.

Figure 2C:

FIG. 2C shows an example of the Retardation map of the optic disk portion. In the drawing, dense shading locations represent small phase differences, and sparse shading locations represent large phase differences. At the optic disk portion, a layer having birefringence is a retinal nerve fiber layer (RNFL), and the Retardation map shows the phase differences caused by the birefringence of RNFL and the thickness of RNFL. Therefore, at the part where RNFL is thick, the phase difference is large; and, at the part where RNFL is thin, the phase difference is small. Therefore, the thickness of RNFL of the entire eye fundus can be perceived by the Retardation map, and this can be used for diagnosis of glaucoma.

<Birefringence Map Generation>

The signal processing unit 190 subjects the value of Retardation δ in the range from ILM to the retinal nerve fiber layer (RNFL) in each A-scan image of the previously generated Retardation image, and determines the tilt thereof as birefringence at the position on the retina of the A-scan image. A map representing birefringence is generated by carrying out this process with respect to all the acquired Retardation images.

Figure 2D:
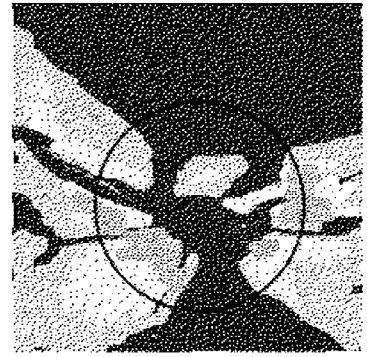

FIG. 2D shows an example of the birefringence map of the optic disk portion. The birefringence map is obtained by directly converting the values of birefringence into map. Therefore, even in the case in which the thickness of RNFL is not changed, if the fiber structure thereof is changed, it can be drawn as change of birefringence.

<Axis Orientation Image Generation>

The signal processing unit 190 calculates the phase difference ΔΦ of each signal from phases $\Phi_H$ and $\Phi_V$, and θ of Axis Orientation is calculated by Expression 4 from the phase difference ΔΦ.

$$\Delta\Phi = \Phi_V - \Phi_H \quad \text{(Expression 3)}$$

$$\theta = \frac{\pi - \Delta\Phi}{2} \quad \text{(Expression 4)}$$

An Axis Orientation image is generated by carrying out this process with respect to all pixels. In a case in which anisotropy is present in a certain structure, Axis Orientation is a parameter which represents the direction of the anisotropy. For example, at the retina, fascicles of nerve fibers of the retinal nerve fiber layer are radially spread about the optic disk. The nerve fiber fascicles are the tissues having anisotropy and have different refractive indexes in course directions and in the direction perpendicular to the courses. Therefore, in a case in which light enters the nerve fiber fascicle, the component in the course direction of the nerve fiber fascicle is retarded with respect to the component perpendicular to the course. In this case, the direction in which propagation of light is retarded, in other words, the course direction of the nerve fiber fascicle serves as a retardation axis, and the direction perpendicular thereto serves as a fast axis. Therefore, the information of the course directions of the nerve fiber fascicles which cannot be distinguished by luminance tomographic images can be obtained from Axis Orientation.

<DOPU Image Generation>

The signal processing unit 190 calculates a Stokes vector S for each pixel by Expression 5 from the acquired tomographic signals $A_H$ and $A_V$ and the phase difference ΔΦ therebetween.

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\Phi \\ 2A_H A_V \sin\Delta\Phi \end{pmatrix} \quad \text{(Expression 5)}$$

Then, the signal processing unit 190 sets, for each B-scan image, a window having a size of about 70 μm approximately in a main scanning direction of measurement light and 18 μm in a depth direction, averages elements of Stokes vectors calculated respectively for pixels in each window by Expression 6, and calculates uniformity DOPU (Degree Of Polarization Uniformity) of polarization in the window by Expression 6.

$$DOPU = \sqrt{Q_m^2 + U_m^2 + U_m^2 + V_m^2} \qquad \text{(Expression 6)}$$

Figure 2E:
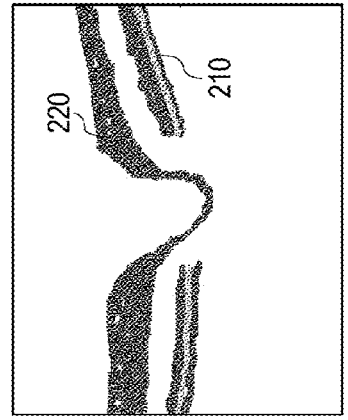

Herein, $Q_m$, $U_m$, and $V_m$ are the average values of elements Q, U, and V of the Stokes vectors in each window. A DOPU image (also referred to as a tomographic image showing uniformity of polarization) shown in FIG. 2E of the optic disk portion is generated by carrying out this process with respect to all the windows in the B-scan image.

DOPU is a numerical value representing the uniformity of polarization, becomes a numerical value close to 1 at the part where polarization is maintained, and becomes a numerical value smaller than 1 at a depolarized part. Since the structure in the retina has a property that RPE cancels the polarization state, the part corresponding to RPE in the DOPU image correspondingly has small values compared with other regions. In the view, a sparse shading location 210 represents RPE, and a dense shading location 220 represents a retina layer region in which changes are maintained. Since the DOPU image converts the layer which cancels polarization such as RPE into image, even in a case in which RPE is deformed due to illness or the like, RPE can be reliably converted into image more than changes of luminance.

Note that, in the present specification, the above described tomographic images corresponding to the first and second polarization, the Retardation image, the DOPU image, etc. will be also referred to as tomographic images showing polarization states. In the present specification, the above described Retardation map, the birefringence map, etc. will be also referred to as eye-fundus images showing polarization states.

[Processing Operation]

Next, processing operations by the present embodiment of the image processing device will be described. This process is operations for distinguishing fibrosed regions and depolarization regions in polarization OCT images and confirming results. FIG. 3 is a flow chart showing a processing operation of the present embodiment of the image processing device. FIG. 3B shows a flow for describing image analysis of step S303 of FIG. 3A.

<Step S301>

In step S301, an unshown subject-eye-information acquiring unit acquires an examinee identification number from outside as the information which identifies a subject eye. Then, by using the information about the examinee identification number, information about the subject eye retained by an unshown storage unit is acquired. Herein, the information about the subject eye means personal information such as a name, gender, age, and medical history; image data such as eye-fundus images and tomographic images; and analysis data of image analysis, etc.

<Step S302>

When an operator specifies an image-taking order button by a cursor displayed on a screen by using an ordering device (not shown) such as a mouse and gives an order by a clicking operation or the like, a tomographic image is taken. Note that the mouse of the present embodiment is provided with, for example, a sensor which detects a movement signal when a mouse main body is two-dimensionally moved by the hand of the operator, left/right two mouse buttons for detecting pressing by the hand of the operator, and a wheel mechanism which is between the left/right two mouse buttons and can be rotated to the front, rear, left, and right. Moreover, the ordering device may mount a touch-panel function in a display unit to carry out image-taking orders on a touch panel or may mount a joystick on a device main body to carry out image-taking orders by the joystick.

In the image-taking, measurement light is emitted from the light source 101 and the light source 141, the light returned from the retina Er is received by the line cameras 129 and 133 and the APDs 152 and 153, and images are generated in the above described manner by the signal processing unit 190.

<Step S303>

The image analyzing unit 193 carries out various analysis with respect to the images generated by the above described signal processing unit 190. The image analyzing unit 193 includes the image generating unit 194, the detection unit 195, and the judgement unit 196. Herein, regarding detection and distinguishment of fibrosed regions and subretina high-luminance regions from Retardation images and DOPU images, operations of the processing units thereof will be described by using FIG. 3 to FIG. 6.

<Step S331>

Figure 4A:
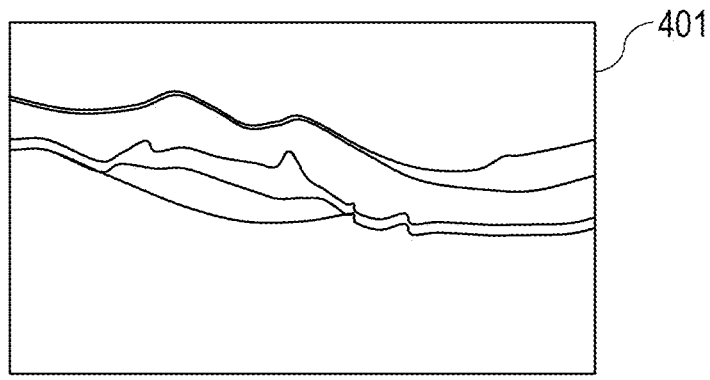
FIGS. 4A to 4C are views for describing image analysis in the first embodiment.
Figure 4B:
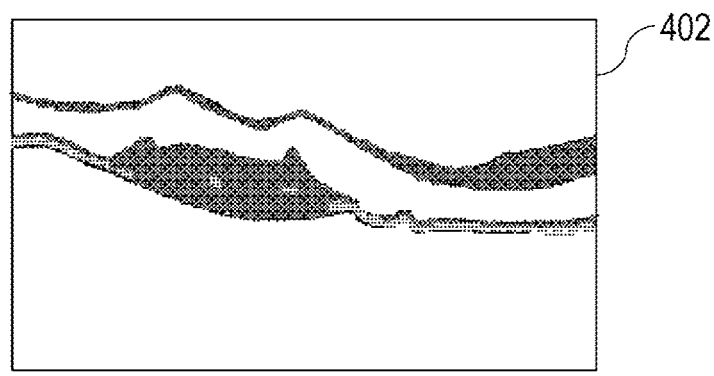
Figure 4C:
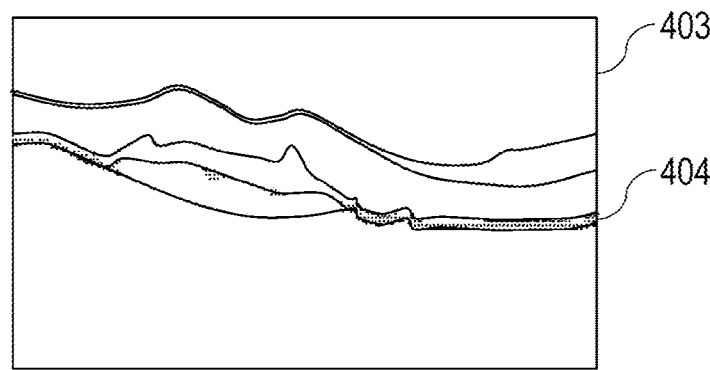

FIGS. 4A, 4B, 4C are views for describing detection of depolarization regions from DOPU images. "401" in FIG. 4A represents a luminance image, and "402" in FIG. 4B represents a DOPU image, which corresponds to the luminance image of FIG. 4A and is obtained by the above described DOPU calculation.

First, the image generating unit 194 obtains depolarized regions from the DOPU image 402. The depolarized regions in the DOPU image 402 have a characteristic that the value thereof is smaller than 1. Therefore, the DOPU image can be separated into the regions in which polarization is maintained and the depolarized regions by subjecting the DOPU image to threshold-value processing (for example, a threshold value of 0.75).

Then, the image generating unit 194 distinguishes depolarized regions. In order to distinguish RPE with respect to the depolarized regions, a RPE estimate curve is obtained. Herein, an example in which the estimate curve is obtained as a quadratic curve (Expression 7) is shown. The curve is obtained by setting an initial curve so that it passes through a large region of the depolarized region and estimating coefficient parameters (a, b, c) of the curve by using a robust estimation method (M estimation or the like). The estimation method of the curve is not limited thereto, but may be estimation of an N-th order curve, or a spline curve may be used.

$$y = ax^2 + bx + c \qquad \text{(Expression 7)}$$

Then, based on the RPE estimate curve, the image generating unit 194 distinguishes an RPE region and the depolarized regions (choroidal tissues, hard exudate region) other than that. The depolarization region present in the region through which the RPE estimate curve passes is assumed to be RPE. In other words, if the RPE estimate curve is passing through part of the region coupled to the depolarization region, the region and therearound is determined as RPE. Then, the depolarization region present in a deep portion of the RPE region is assumed to be a Choroid (choroidal tissue) region, and the depolarization region present in a shallow portion in the region is assumed to be a Particle (hard exudate) region. An image 403 in which a depolarization region 404 obtained by these is superimposed on the luminance image 401 is shown in FIG. 4C.

<Step S332>

Figure 5A:
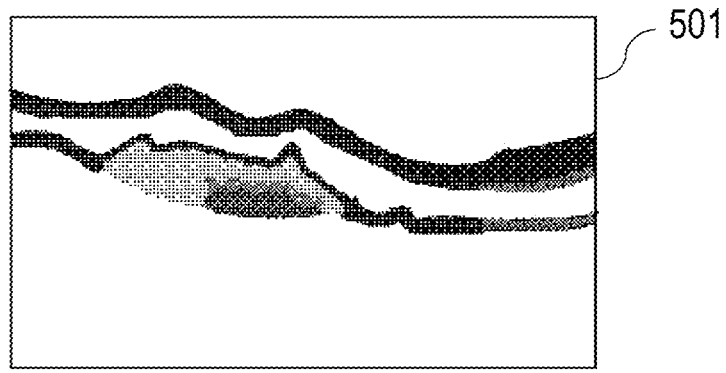
FIGS. 5A and 5B are views for describing image analysis in the first embodiment.
Figure 5B:
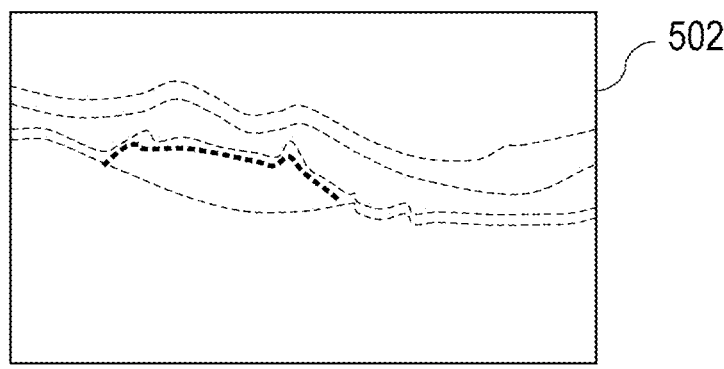

Then, the image generating unit 194 obtains the gradient in the A-scan direction with respect to the Retardation image in order to extract the part having high birefringence from the Retardation image. This will be described by using FIGS. 5A and 5B. "501" in FIG. 5A represents a Retardation image, and "502" in FIG. 5B represents a gradient image of phase retardation information, wherein the gradient in the depth direction is obtained with respect to the Retardation image. Herein, the gradient image is an example of a polarization tomographic image showing a change amount of the phase retardation information. The Retardation image 501 may be a Retardation image using a single image of B-scan or may be a Retardation image obtained by subjecting B-scan of a plurality of times taken at the same part to averaging processing. The image generating unit 194 obtains the gradient of the Retardation image 501 and generates a gradient image. Note that the present embodiment is not required to obtain the gradient image, and, in that case, a process of repeating steps for each A-scan in steps S333 to S338 is carried out. The gradient image may be displayed by a monitor in a form as shown in FIG. 5B. The boundary of the fibrosed region is more easily observed in the gradient image than in the Retardation image. In this case, the gradient image may be only displayed by the monitor without executing the processes of steps S333 to S338.

Herein, in order to obtain the gradient, for example, a Sobel filter is used. Since the changes in Retardation desired to be obtained in this process are in the depth direction (z-direction) of the image of A-scan, a filter for obtaining the differences in the direction perpendicular to the image is applied. Note that the matter to obtain the gradient is not limited to the Sobel filter, but may be a Prewitt filter or a difference between the pixels adjacent to each other in the z-direction.

<Step S333>

Figure 6:
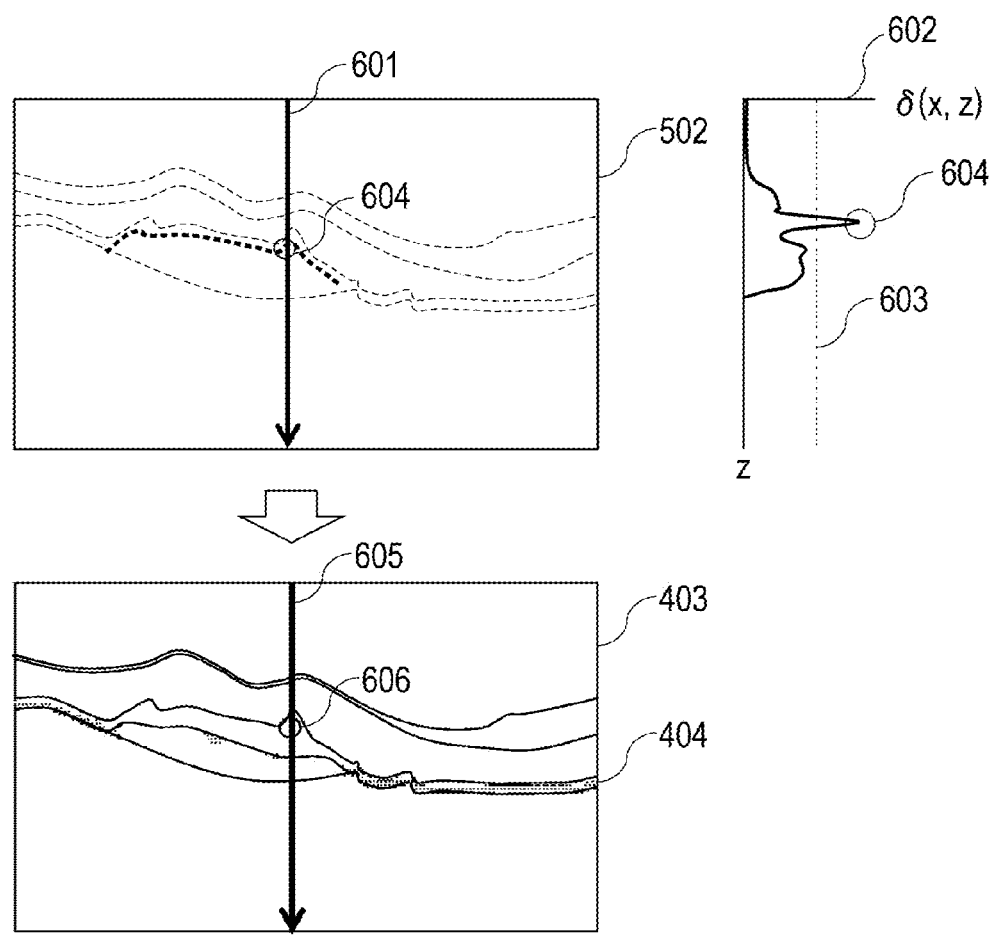
FIG. 6 is a view for describing image analysis in the first embodiment.

In step S333 to step S338, detection and distinguishment of a fibrosed region and a subretina high-luminance region is carried out by using the Retardation gradient image 502 and the depolarization region 404 obtained from the DOPU image 402. This will be described by using FIG. 6. In FIG. 6, "601" represents an arbitrary A-scan part in the Retardation gradient image 502. "602" represents a Retardation gradient profile of A-scan 601. "603" represents the threshold value in the gradient profile 602. "604" represents a part equal to or more than the threshold value (region in which the change amount of the phase retardation information is equal to or more than the threshold value) in the gradient profile 602. "605" represents A-scan at the same location as A-scan 601 in the image 403. "606" represents an example showing the part 604, which is equal to or more than the threshold value in the gradient profile, in the image 403.

In step S333, the detection unit 195 detects the value of gradient at each pixel of A-scan from the Retardation gradient image 502. The profile of the gradient acquired in this process is 602.

<Step S334>

In step S334, the judgement unit 196 judges whether the gradient of Retardation acquired in step S333 is equal to or more than the threshold value. Since Retardation is changed in the range of 0° to 90°, for example, the threshold value is set to 15°. If the gradient is equal to or more than the threshold value, the process proceeds to step S335; and, if the gradient is less than the threshold value, the process proceeds to step S338. When the region in which the change amount of the phase retardation information is equal to or more than the threshold value is detected, noise component, etc. derived by the optical system, etc. of the device included in the Retardation image can be reduced. Therefore, viewing of the fibrosed region can be further facilitated. Note that, in a case in which the above described noise component is comparatively small, step 335 to step 338 are not required to be executed, in that sense, these processes are not essential processes.

<Step S335>

In step S335, in the part in which the Retardation gradient is equal to or more than the threshold value, the judgement unit 196 carries out judgement whether the part is a depolarization region 404 or not. If it is the depolarization region 404, the process proceeds to step S336; and, if it is not the depolarization region 404, the process proceeds to step S337.

<Step S336>

In step S336, the judgement unit 196 judges that it is a depolarization region since there is a high possibility that the region is scattered RPE or hard exudate even if the Retardation gradient is equal to or more than the threshold value.

<Step S337>

In step S337, the judgement unit 196 assumes that there is a possibility that this is fibrosed since this region has the Retardation gradient equal to or more than the threshold value and is not the depolarization region 404. Note that changes of Retardation are increased as it advances in the birefringence region. More specifically, a part in the course of change of Retardation is a tissue having birefringence. Therefore, by using a fibrosed candidate point obtained in this process as a starting point, the detection unit 195 detects the part in which gradient is large in the range of several tens of pixels in a shallow-portion direction of A-scan (upward direction of tomographic image) in the luminance image 403. The range of fibrosed region may be determined by this.

<Step S338>

In step S338, the judgement unit 196 determines whether all the processes of A-scan have been finished or not. For example, if the number of A-scan is 1024, the process is carried out 1024 times. If all the processes of A-scan have not been finished, a similar process is carried out in next A-scan. If they have been finished, the flow of analysis is finished, and the process proceeds to a display process of step S304.

<Step S304>

When the generation and analysis of the images are finished in the signal processing unit 190 and the image analyzing unit 193, based on the results thereof, the display control unit 191 generates output information and output that to the display unit 192 to carry out display.

Figure 7:
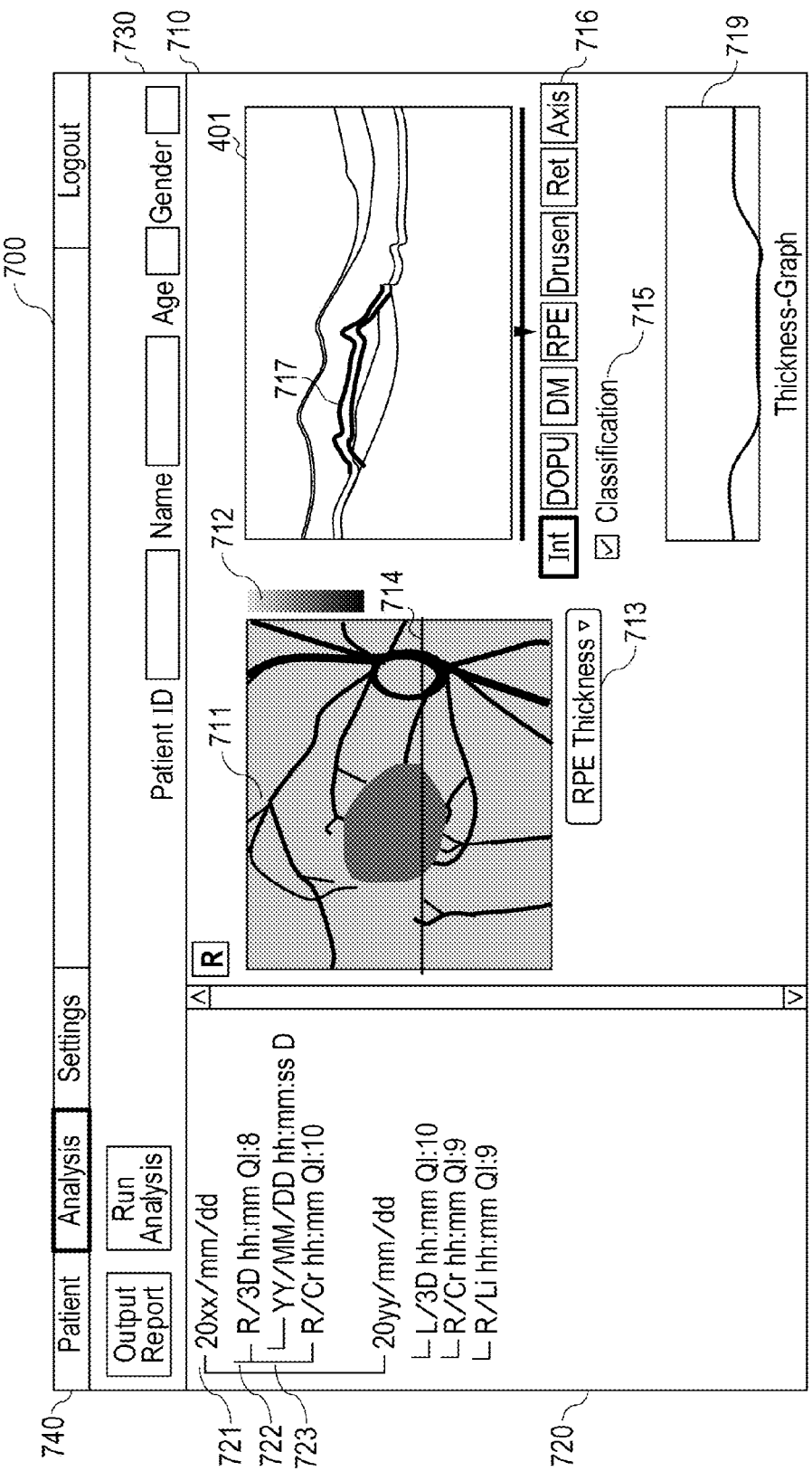
FIG. 7 shows a display example of a display screen of a display unit of the image processing device in the first embodiment.

FIG. 7 is a display example at the display unit 192 in the present embodiment. In the view, "700" represents a window displayed by the display unit 192, and the window has display regions 710, 720, 730, and 740. The display region 710 has an eye-fundus planar image and analysis map (Enface) image display 711, a color bar 712 for showing the thickness of the map by colors, a selecting part 713 of the eye-fundus planar image and the analysis map, and an index 714 for showing the position of the tomographic image in the map. A tomographic image region shows a check box 715 for displaying the results analyzed by the image analyzing unit 193, the tomographic image 403, the depolarization region 404, a tomographic-image selecting part 716, and a thickness graph 719.

The selecting part 713 of the eye-fundus planar image and the analysis map can switch display of Pseudo SLO, a DM thickness map, a RPE thickness map, a drusen thickness map, a GA map, a Retardation map, a birefringence map, etc. The tomographic-image selecting part 716 can switch display of a luminance image, a DOPU image, a DM (Depolarizing Material) image, a RPE image, a Drusen image, a Retardation image, and an Axis Orientation image. Herein, the DM image, the RPE image, and the Drusen image are subjected to superimposition display of the thing obtained from the depolarization region with the luminance image. The thickness of the thickness map is displayed by colors as shown by the color bar of 712. In the present embodiment, the thickness is expressed so that, the deeper the color, the smaller the thickness of the map; and, the paler the color, the larger the thickness of the map. In the RPE thickness map 711 of FIG. 7, a deep-color region in the vicinity of the center represents a location without RPE.

Note that the present embodiment shows an example in which the results of analysis by the image analyzing unit 193 are displayed (the check box 715 is ON). If the luminance image is selected by the tomographic-image selecting part 716, the luminance image serves as the image which serves as a basis of display, and a fibrosed region 717 is displayed to be superimposed thereon as the result of the analysis by the image analyzing unit 193. Note that, as long as the boundary of the fibrosed region can be distinguished, any display mode may be used. The tomographic image which serves as the basis of the display can be switched by the tomographic-image selecting part 716, and the fibrosed region 717 can be displayed to be superimposed on the Retardation image. Although it is not shown in the view, instead of the graph 719, the Retardation gradient image 502 may be displayed in juxtaposition. The gradient image 502 in that case is desired to be displayed by colors. Furthermore, only the regions of the threshold value or more may be displayed by colors instead of showing all of the gradient image 502 by colors.

The display region 720 shows a tree of inspection data. "721" represents image-taken date, "722" represents image-taking information (left/right eye, scan pattern, image-taken time), and "723" represents analysis time and an analysis mode.

The display region 730 displays patient information (identification information, name, age, gender). Note that the display of the patient information is not limited thereto, and other information may be displayed.

The display region 740 displays information that distinguishes the screen that is in operation. In the present embodiment, a patient-data management screen, an analysis screen, and a setting screen are displayed. In the present embodiment, the region 740 is not only displayed, but is also provided with a selecting function, and functions can be switched by selecting locations in the region 740.

The thickness graph 719 is interlocked with the analysis map 711. Note that the types of the images displayed in the analysis map and the tomographic image can be independently selected, but are not limited to be so, and they may be displayed to be interlocked. For example, if the DM image is selected for the tomographic image, the analysis map image may display the DM thickness map.

<Step S305>

In step S305, finish of analysis result confirmation is selected. When the result confirmation is finished or when the process undergoes a transition to select an image-taking mode, manual correction results obtained in the processes up to this point and the analysis results by the image analyzing unit 193 are saved in the storage unit.

As described above, according to the present embodiment, a mechanism that carries out distinguishment and result confirmation of the fibrosed region and depolarization region in the polarization OCT image is provided. Note that the present embodiment shows the example in which the fibrosed region and the depolarization region are analyzed, but is not limited thereto. As an image analysis mode, a Drusen analysis mode, a GA analysis mode, a Glaucoma analysis mode, an analysis mode supporting diseases, a Full analysis mode in which all processes are executed, etc. can be selected.

Second Embodiment

In the first embodiment, the example, in which fibrosed region and the depolarization region are distinguished by using the Retardation image and the DOPU image, has been shown. In the present embodiment, an example in which a fibrosed region, a depolarization region, and a new blood vessel are distinguished by combination with an Axis Orientation image will be described.

Herein, the description of those having similar functions as those of the above described first embodiment is omitted. In the present embodiment, the processing in the image analyzing unit 193 is different; and, in the process flow, the processing method of the image analysis of step S303 of FIG. 3 is different. Hereinafter, description will be given by using FIG. 8 to FIG. 10.

Figure 8:
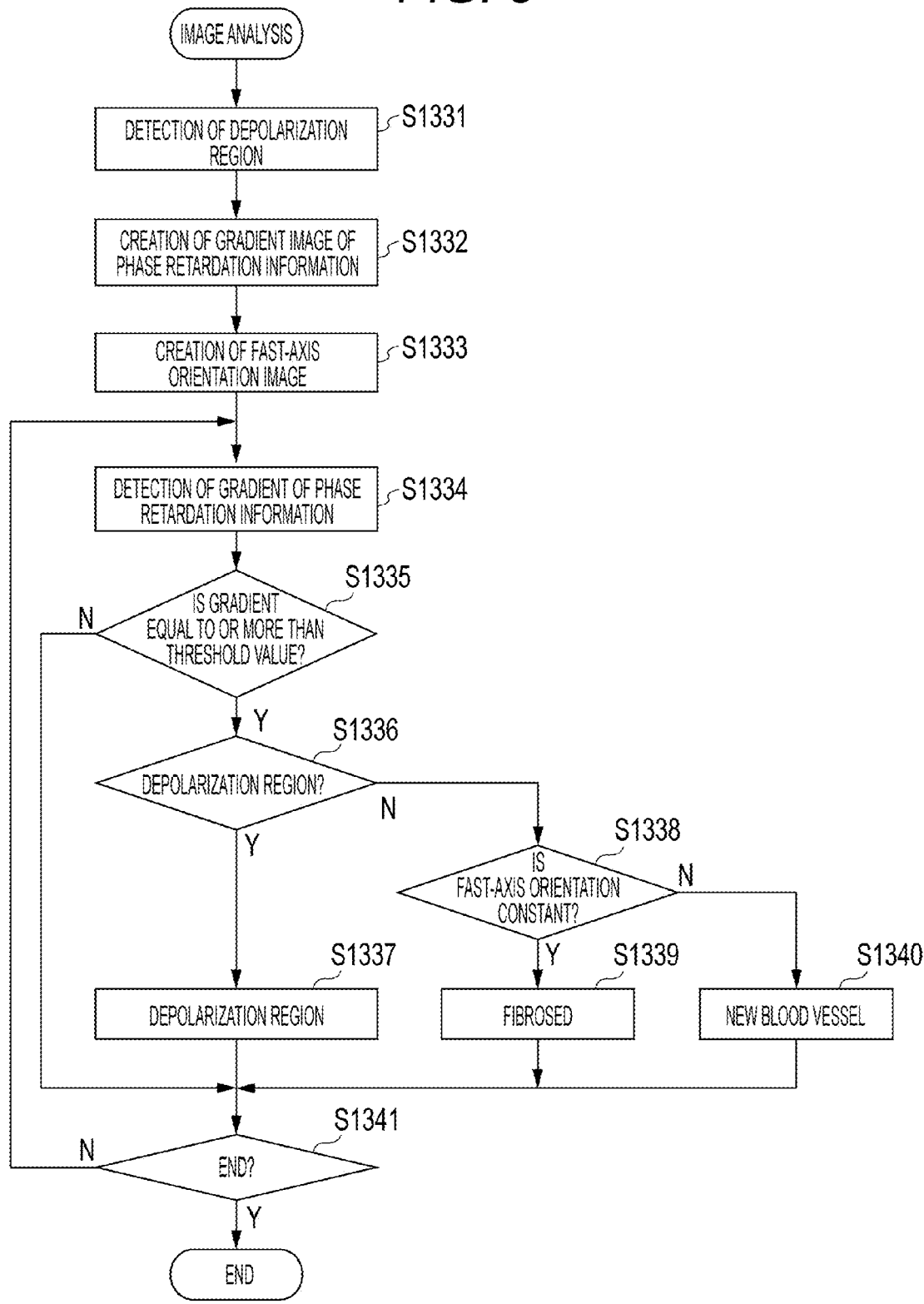
FIG. 8 shows a process flow in a second embodiment.

FIG. 8 shows a process flow in the second embodiment. In the image analysis of step S303 of the present embodiment, the image analyzing unit 193 carries out various analysis with respect to the images generated by the above described signal processing unit 190. Herein, detection and distinguishment of a fibrosed region, a depolarization region, and a new blood vessel from a Retardation image, a DOPU image, and an Axis Orientation image will be described. Note that steps S1331 and S1332 are similar to those of the first embodiment and are therefore omitted.

<Step S1333>

Figure 9A:
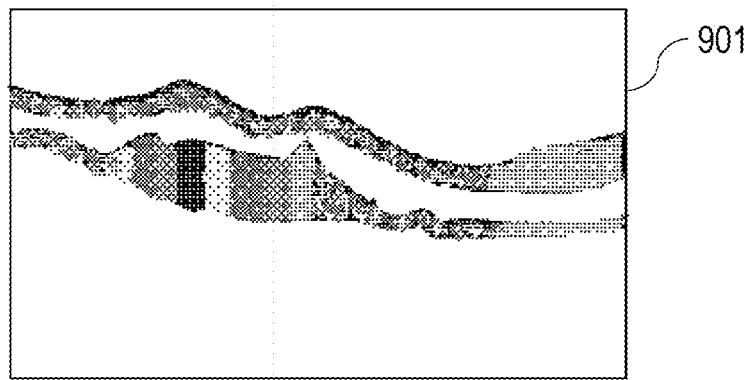
FIGS. 9A and 9B are views for describing image analysis in the second embodiment.

In a fibrosed region in the retina layer, the directions of fibers are aligned in a certain direction. Therefore, in a fibrosed part in the Axis Orientation image, values of aligned fast-axis orientations (fast-axis-orientation information) can be observed. Therefore, in step S1333, in order to extract the region in which the fast-axis orientations are aligned, a process of extracting variation degrees in spatial values is carried out with respect to the Axis Orientation image. This will be described by using FIG. 9. "901" in FIG. 9A represents an Axis Orientation image. The Axis Orientation image 901 may be an Axis Orientation image using a single image of B-scan or may be an Axis Orientation image obtained by subjecting B-scan of a plurality of times taken at the same part to averaging processing. The image generating unit 194 generates an image to obtain dispersions of the fast-axis orientations with respect to the Axis Orientation image 901. In order to obtain dispersions, the Axis Orientation image is subjected to scanning of the entire image by ROI of M×N size. For example, following Expression 8 is used for the dispersion of the image. In Expression 8, "(i, j)" represents a pixel coordinate, "f(i, j)" represents a fast-axis orientation of the pixel, and "μ" represents an average value of the fast-axis orientation of ROI of the M×N size.

$$\sigma^2 = \frac{1}{M \times N} \sum_{j=0}^{N-1} \sum_{i=0}^{M-1} (f(i, j) - \mu)^2 \qquad \text{(Expression 8)}$$

Figure 9B:
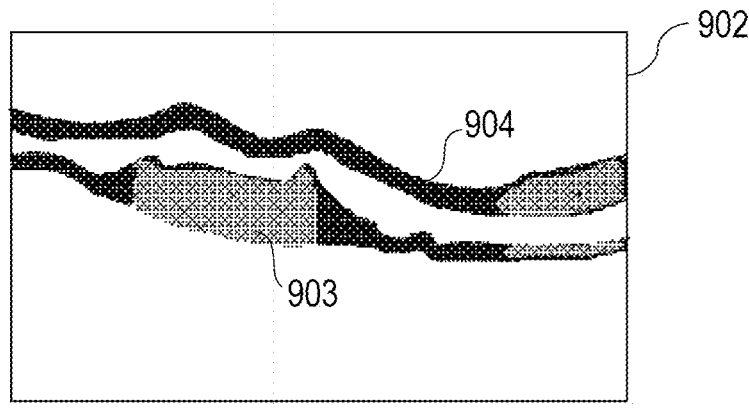

"902" in FIG. 9B represents the image which has undergone threshold-value processing of the dispersion value, wherein the dispersion value is calculated by ROI of the M×N size (for example, 50×20 μm). In FIG. 9B, the location at which the dispersion value is equal to or less than the threshold value is represented by 903, and the location at which the dispersion value is equal to or more than the threshold value is represented by 904. Therefore, the region 903 in which the dispersion value is low in ROI having a certain size represents the region in which the fast-axis orientations are aligned. Note that FIG. 9B is a binary image in which the dispersion value is equal to or more than or less than the threshold value. However, the region equal to or less than the threshold value may have a ROI average value of the M×N size or the original value of the fast-axis orientation of the pixel.

Next, since steps S1334 to S1337 are the same as steps S333 to S336 of the first embodiment, the description thereof is omitted.

<Step S1338>

Figure 10:
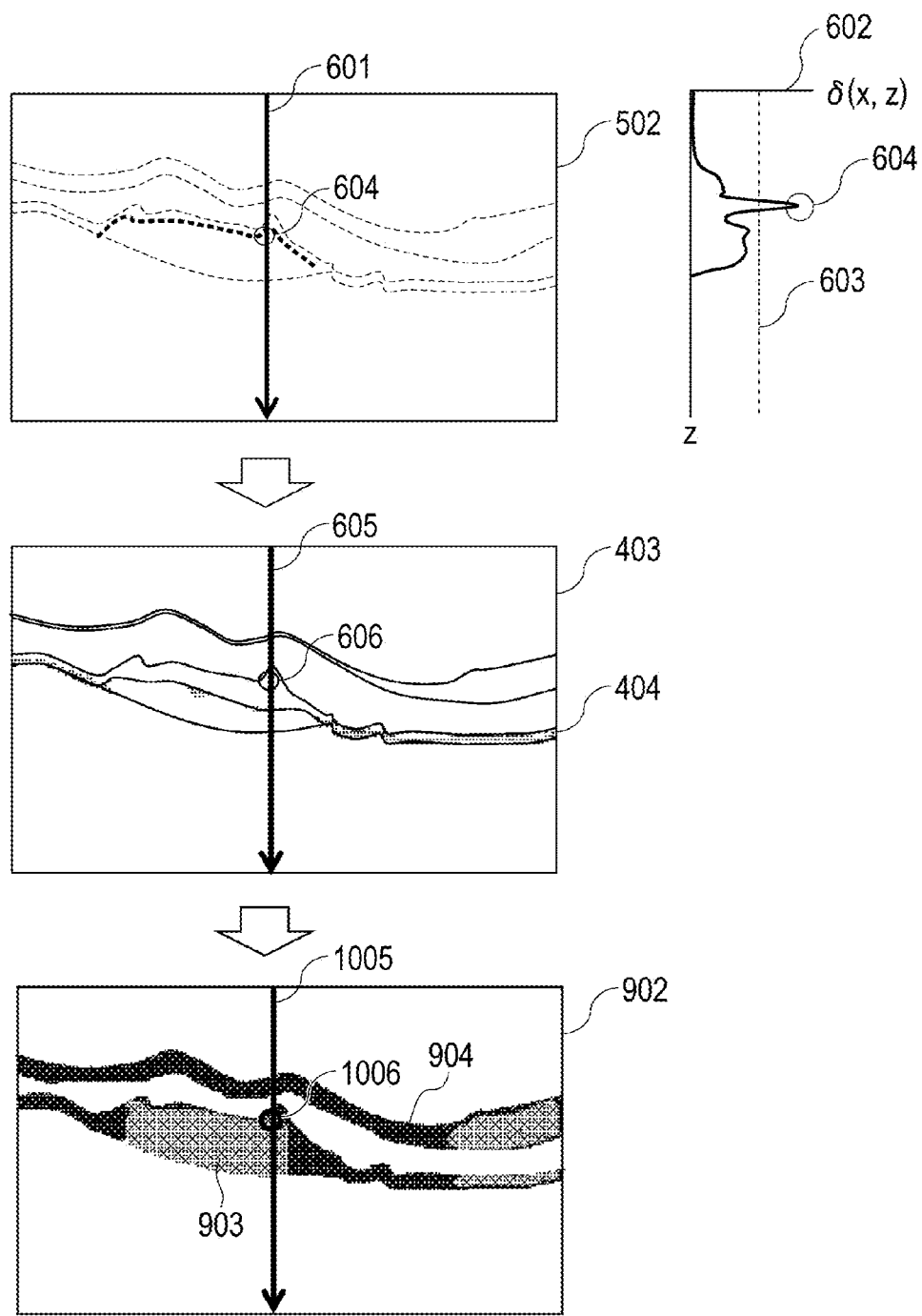
FIG. 10 is a view for describing image analysis in the second embodiment.

In step S1338, the judgement unit 196 judges whether the fast-axis orientations are aligned. This will be described by using FIG. 10. Since part of FIG. 10 is the same as FIG. 6, differences will be described herein. FIG. 10 is an example in which, in an image 902, "1005" represents A-scan at the same location as A-scan 601, and "1006" represents, in the image 902, a part 604 which is equal to or more than the threshold value in the gradient profile.

The judgement unit 196 checks whether the part at which a change in the gradient profile 602 is equal to or more than the threshold value in step S1335 is a depolarization region 404 or not in step S1336. If it is not the depolarization region 404, in step S1338, whether the fast-axis orientations are a constant orientation or not is checked in the dispersion image 902 of Axis Orientation. If the fast-axis orientations are aligned, the process proceeds to step S1339. If the fast-axis orientations are not aligned, the process proceeds to step S1340.

<Step S1339>

In step S1339, the judgement unit 196 assumes there is a possibility that the region has fibrosed since the region has the Retardation gradient equal to or more than the threshold value, is not the depolarization region 404, and have the aligned fast-axis orientations of Axis Orientation. Note that changes of Retardation are increased as it advances in the birefringence region. More specifically, a part in the course of change of Retardation is a tissue having birefringence. Therefore, by using a fibrosed candidate point obtained in this process as a starting point, the detection unit 195 detects the part in which gradient is large in the range of several tens of pixels in a shallow-portion direction of A-scan (upward direction of tomographic image) in the luminance image 403. The range of fibrosed region may be determined by this.

<Step S1340>

In step S1340, the judgement unit 196 judges that there is a possibility of a new blood vessel since the region has the Retardation gradient equal to or more than the threshold value, is not the depolarization region 404, and does not have aligned fast-axis orientations of Axis Orientation.

As described above, according to the present embodiment, distinguishment and result confirmation of the fibrosed region, the depolarization region, and the new blood vessel in the polarization OCT image can be carried out.

Third Embodiment

The second embodiment shows the example in which the fibrosed region, the depolarization region, and the new blood vessel are distinguished by using the Retardation image, the DOPU image, and the Axis Orientation image. In the present embodiment, an example in which a fibrosed region and a new blood vessel are distinguished from an Intensity image, a DOPU image, and an Axis Orientation image will be described.

The description of those having similar functions as the above described first and/or second embodiments will be omitted herein. In the present embodiment, processing in the image analyzing unit 193 is different, and, in the process flow, the processing method of the image analysis of step S303 of FIG. 3 is different. Hereinafter, description will be given by using FIG. 11 and FIG. 12.

Figure 11:
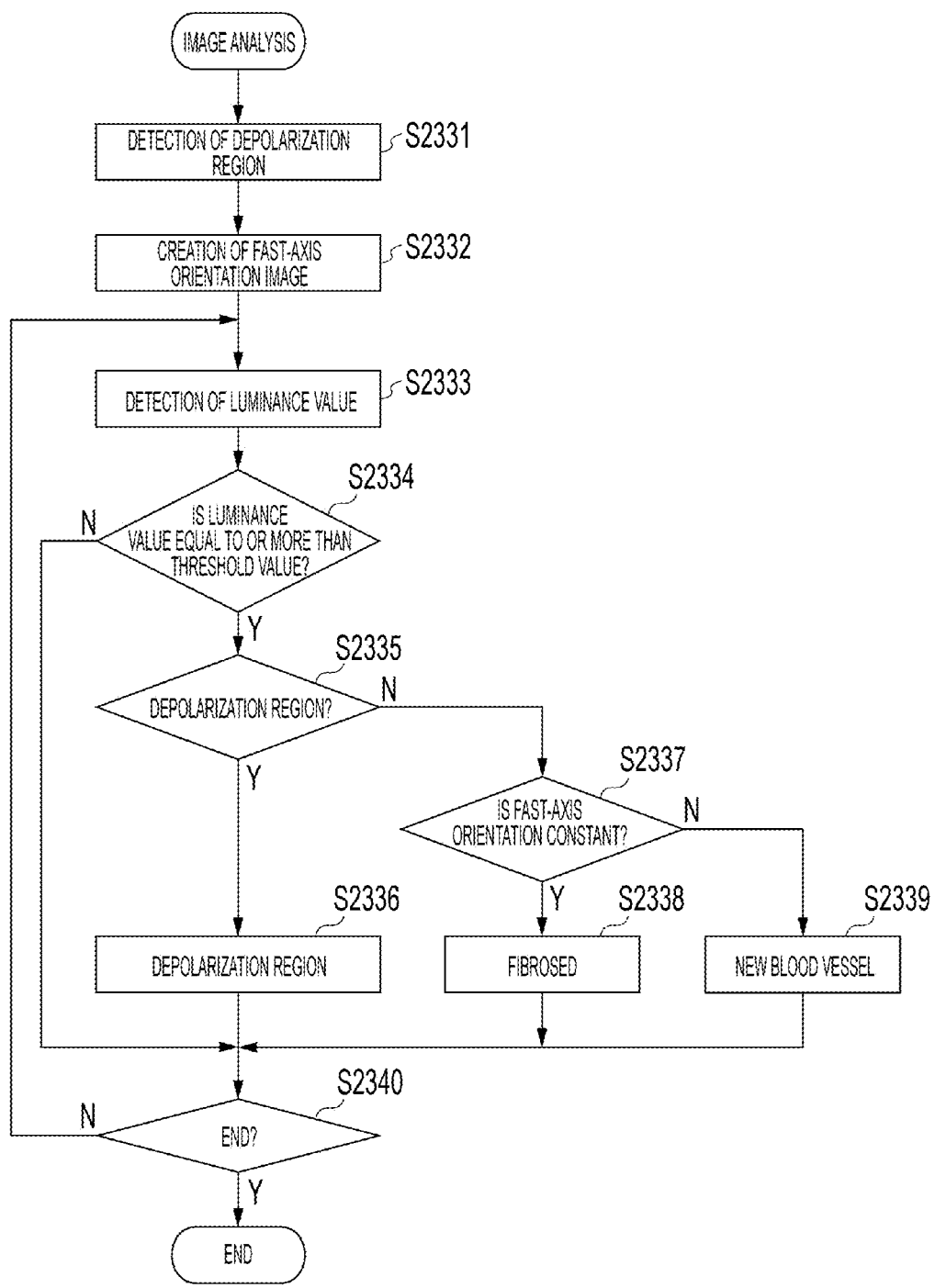
FIG. 11 shows a process flow in a third embodiment.

FIG. 11 shows a process flow in a third embodiment. In the image analysis of step S303 of the present embodiment, the image analyzing unit 193 carries out various analysis with respect to the images generated by the above described signal processing unit 190. Herein, detection and distinguishment of a fibrosed region, a depolarization region, and a new blood vessel from an Intensity image, a DOPU image, and an Axis Orientation image will be described. Note that step S2331 will be omitted since it is similar to step S331 of the first embodiment, and S2332 will be omitted since it is similar to step S1333 of the second embodiment.

<Step S2333>

From step S2333 to step S2340, detection and distinguishment of a fibrosed region and a subretina high-luminance region is carried out by using the Intensity image 401, the depolarization region 404, and the dispersion image 902 of fast-axis orientations. In step S2333, the detection unit 195 detects the luminance vale of each pixel of A-scan from the Intensity image 401.

<Step S2334>

In step S2334, the judgement unit 196 judges whether the luminance value of the Intensity image acquired in step S2333 is equal to or more than the threshold value. If the luminance value is equal to or more than the threshold value, the process proceeds to step S2335; and, if the luminance value is less than the threshold value, the process proceeds to step S2340.

<Step S2335>

In step S2335, at the part in which the luminance value of the Intensity image is equal to or more than the threshold value, the judgement unit 196 judges whether that part is a depolarization region 404 or not. If that part is the depolarization region 404, the process proceeds to step S2336. If that part is not the depolarization region 404, the process proceeds to step S2337.

<Step S2336>

In step S2336, even if the luminance value of the Intensity image is equal to or more than the threshold value, the judgement unit 196 judges that it is a depolarization region.

<Step S2337>

Figure 12:
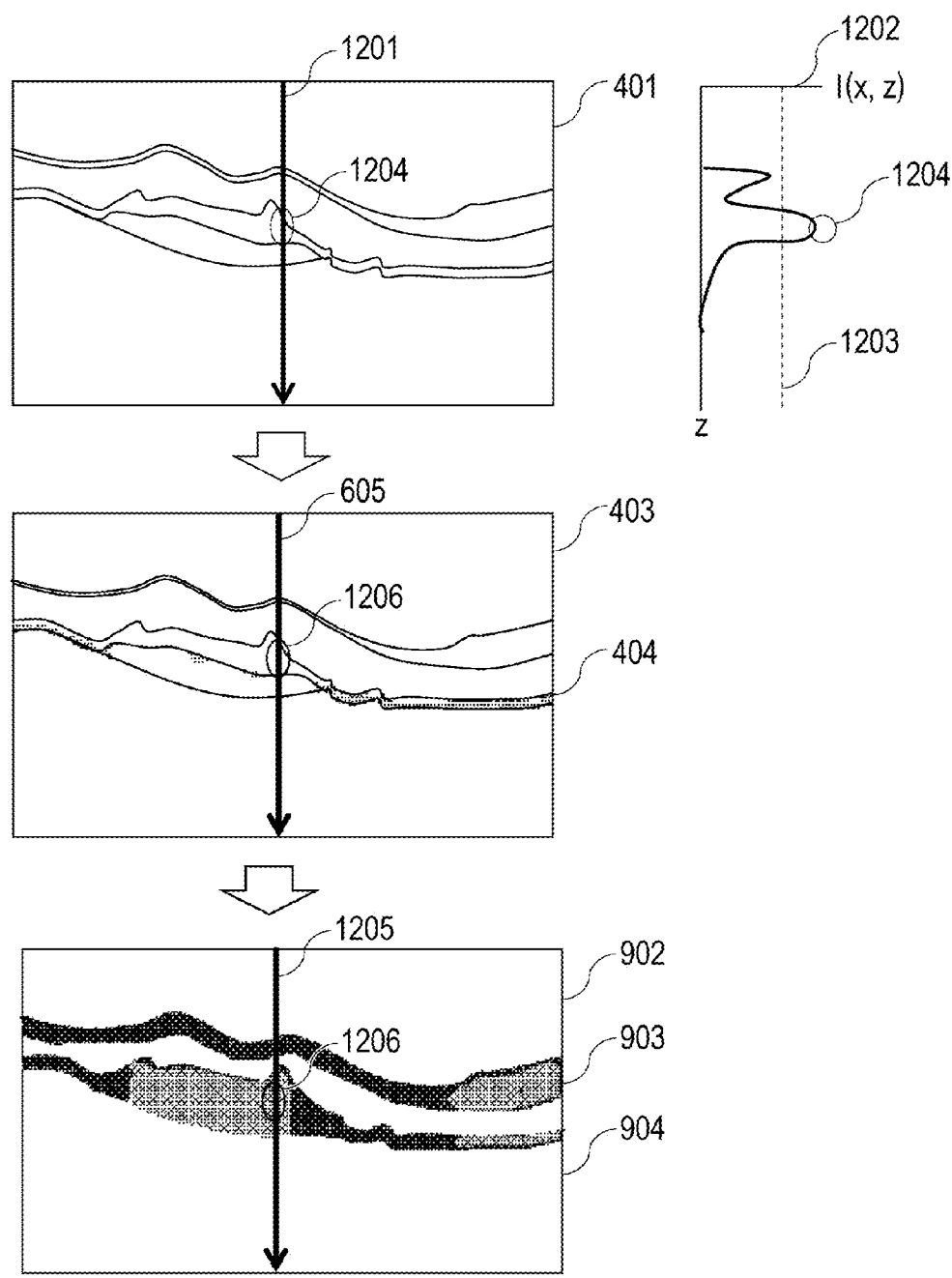
FIG. 12 is a view for describing image analysis in the third embodiment.

In step S2337, the judgement unit 196 judges whether fast-axis orientations are aligned or not. This will be described by using FIG. 12. In FIG. 12, "1201" represents an arbitrary A-scan part in the Intensity image 401, "1202" represents a luminance profile of Intensity at the A-scan 1201, "1203" represents a threshold value in the luminance profile, and "1204" represents the part which is equal to or more than the threshold value in the luminance profile 1202. "605" represents A-scan at the same location as the A-scan 1201 in the image 403, "1206" shows the part 1204, which is equal to or more than the threshold value in the luminance profile, in the image 403, "1205" represents A-scan at the same location as the A-scan 1201 in the image 902, and "1216" is an example showing the part 1204, which is equal to or more than the threshold value in the luminance profile, in the image 902.

At the part at which the change in the luminance profile 1204 is equal to or more than the threshold value in step S2334, the judgement unit 196 checks in step S2335 whether it is the depolarization region 404 or not. If it is not the depolarization region 404, in step S2337, whether the fast-axis orientations are constant orientations or not is checked in the dispersion image 902 of Axis Orientation. If the fast-axis orientations are aligned, the process proceeds to step S2338. If they are not aligned, the process proceeds to step S2339.

<Step S2338>

In step S2338, the judgement unit 196 assumes that this region has fibrosed since this region has the luminance value of the Intensity image equal to or more than the threshold value, is not the depolarization region 404, and has aligned fast-axis orientations of Axis Orientation.

<Step S2339>

In step S2339, the judgement unit 196 judges that there is a possibility of a new blood vessel since the region has the luminance value of the Intensity image equal to or more than the threshold value, is not the depolarization region 404, and does not have aligned fast-axis orientations of Axis Orientation.

As described above, according to the present embodiment, a mechanism that carries out distinguishment and result confirmation of a fibrosed region, a depolarization region, and a new blood vessel in a polarization OCT image is provided.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-016366, filed Jan. 29, 2016, which is hereby incorporated by reference herein in its entirety.

What is claimed is:

1. An image processing device comprising:
at least one memory storing executable instructions; and
at least one processor coupled to the at least one memory and executing the executable instructions to cause the image processing device to:
generate phase retardation information of a subject eye by using information about a plurality of lights obtained by dividing, into lights having different polarizations, a light obtained by combining a light returned from the subject eye irradiated with a measurement light and a reference light corresponding to the measurement light;
detect a first region of the subject eye in which a change amount of the phase retardation information in a depth direction of the subject eye is larger than a threshold value;
detect a second region of the subject eye in which a region is not depolarized in the detected first region as at least one candidate region of fibrosis of the eye; and
output an indication of location of the at least one candidate region to a display unit.

2. The image processing device according to claim 1, wherein the at least one processor executes the executable instructions to cause the image processing device to:
generate a tomographic image of uniformity of polarization of the subject eye by using information about a phase difference of the plurality of lights; and
judge, by using information about the detected region and the tomographic image of the uniformity of the polarization, whether the detected region has fibrosed or has not fibrosed.

3. The image processing device according to claim 2, wherein the at least one processor executes the executable instructions to cause the image processing device to cause a display unit to display a result of such judgement.

4. The image processing device according to claim 1, wherein the at least one processor executes the executable instructions to cause the image processing device to:
generate an image including the detected region superimposed on a luminance tomographic image of the subject eye generated by using the information about the plurality of lights; and
display unit to display the generated image.

5. The image processing device according to claim 1, wherein the at least one processor executes the executable instructions to cause the image processing device to cause a display unit to display a polarization tomographic image showing the change amount of the phase retardation information.

6. An image processing device comprising:
at least one memory storing executable instructions; and
at least one processor coupled to the at least one memory and executing the executable instructions to cause the image processing device to:
generate intensity information of the subject eye by using information about a plurality of lights obtained by dividing, into lights having different polarizations, a light obtained by combining a light returned from the subject eye irradiated with a measurement light and a reference light corresponding to the measurement light;
detect a first region of the subject eye in which a change amount of the intensity information in a depth direction of the subject eye is larger than a threshold value;
detect a second region of the subject eye in which a variation degree of fast axis orientation information is smaller than a threshold value in the detected first region as at least one candidate region of fibrosis of the eye; and
output an indication of location of the at least one candidate region to a display unit.

7. The image processing device according to claim 6, wherein the at least one processor executes the executable instructions to cause the image processing device to detect a region in which the variation degree of the fast-axis orientation information is smaller than a threshold value.

8. The image processing device according to claim 7, wherein the at least one processor executes the executable instructions to cause the image processing device to:
generate a tomographic image of uniformity of polarization of the subject eye by using information about a phase difference of the plurality of lights; and
judge, by using information about the detected region and the tomographic image of the uniformity of the polarization, whether the detected region has fibrosed or has not fibrosed.

9. An image processing method comprising:
generating phase retardation information of a subject eye by using information about a plurality of lights obtained by dividing, into lights having different polarizations, a light obtained by combining a light returned from the subject eye irradiated with a measurement light and a reference light corresponding to the measurement light;
detecting a first region of the subject eye in which a change amount of the phase retardation information in a depth direction of the subject eye is larger than a threshold value;
detecting a second region of the subject eye in which a region is not depolarized in the detected first region as at least one candidate region of fibrosis of the eye; and
outputting an indication of location of the at least one candidate region to a display unit.

10. The image processing method according to claim 9, further comprising:
generating a tomographic image of uniformity of polarization of the subject eye by using information about a phase difference of the plurality of lights; and
judging, by using information about the detected region and the tomographic image of the uniformity of the polarization, whether the detected region has fibrosed or has not fibrosed.

11. The image processing method according to claim 10, further comprising causing a display unit to display a result of the judging.

12. The image processing method according to claim 9, further comprising
generating an image including the detected region superimposed on a luminance tomographic image of the subject eye generated by using the information about the plurality of lights; and
causing a display unit to display the generated image.

13. The image processing method according to claim 9, further comprising causing a display unit to display a polarization tomographic image showing the change amount of the phase retardation information.

14. A non-transitory computer-readable storage medium storing a program that when executed by a computer causes the computer to execute the image processing method according to claim 9.

15. An image processing method comprising:
generating intensity information of the subject eye by using information about a plurality of lights obtained by dividing, into lights having different polarizations, a light obtained by combining a light returned from the subject eye irradiated with a measurement light and a reference light corresponding to the measurement light;
detecting a first region of the subject eye in which a change amount of the intensity information in a depth direction of the subject eye is larger than a threshold value;
detecting a second region of the subject eye in which a variation degree of fast axis orientation information is smaller than a threshold value in the detected first region as at least one candidate region of fibrosis of the eye; and
outputting an indication of location of the at least one candidate region to a display unit.

16. The image processing method according to claim 15, further comprising detecting a region in which the variation degree of the fast-axis orientation information is smaller than a threshold value.

17. The image processing method according to claim 16, further comprising:
generating a tomographic image of uniformity of polarization of the subject eye by using information about a phase difference of the plurality of lights; and
judging, by using information about the detected region and the tomographic image of the uniformity of the polarization, whether the detected region has fibrosed or has not fibrosed.

18. A non-transitory computer-readable storage medium storing a program that when executed by a computer causes the computer to execute the image processing method according to claim 15.

* * * * *